US011420009B2

(12) United States Patent
Arrowsmith et al.

(10) Patent No.: US 11,420,009 B2
(45) Date of Patent: Aug. 23, 2022

(54) VALVE WITH INTERNAL MEMBER

(71) Applicant: Fisher & Paykel Healthcare Limited, Auckland (NZ)

(72) Inventors: Mark John Arrowsmith, Auckland (NZ); Andrew John Partington, Auckland (NZ); Sophia Adele Johnson, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 17/012,447

(22) Filed: Sep. 4, 2020

(65) Prior Publication Data

US 2021/0069456 A1 Mar. 11, 2021

Related U.S. Application Data

(63) Continuation of application No. 16/245,118, filed on Jan. 10, 2019, now Pat. No. 10,792,460, which is a (Continued)

(51) Int. Cl.
*F16K 15/14* (2006.01)
*A61M 16/20* (2006.01)
(Continued)

(52) U.S. Cl.
CPC .......... *A61M 16/208* (2013.01); *A61M 16/20* (2013.01); *F16K 15/145* (2013.01);
(Continued)

(58) Field of Classification Search
CPC ...... F16K 15/144; F16K 15/145; F16K 15/16; Y10T 137/784; Y10T 137/7887;
(Continued)

(56) References Cited

U.S. PATENT DOCUMENTS 2,372,726 A 4/1945 Langdon
2,657,899 A 11/1953 Kohler et al.
(Continued)

FOREIGN PATENT DOCUMENTS

GB 907365 A * 10/1962 ............. E21B 21/10
WO WO 1997/002850 A1 1/1997
(Continued)

OTHER PUBLICATIONS

Written Opinion; PCT/NZ2014/000203; dated Dec. 9, 2014; 5 pages.
(Continued)

*Primary Examiner* — Hailey K. Do
(74) *Attorney, Agent, or Firm* — Knobbe Martens Olson and Bear, LLP

(57) ABSTRACT

A valve with an internal member is disclosed which allows exhaled carbon dioxide to escape from a breathing circuit when the circuit gas pressure drops below a threshold pressure. The valve operates by occluding one or more ports under a relatively high pressure and opening the one or more ports under a relatively low pressure. The internal member is attached to the body of the valve at two or more locations on the internal member. The internal member moves in a direction perpendicular to the gas flow through the valve.

20 Claims, 11 Drawing Sheets

Related U.S. Application Data continuation of application No. 15/022,500, filed as application No. PCT/NZ2014/000203 on Sep. 17, 2014, now Pat. No. 10,213,576.

(60) Provisional application No. 61/912,390, filed on Dec. 5, 2013, provisional application No. 61/879,012, filed on Sep. 17, 2013.

(51) Int. Cl.
| | |
|---|---|
| *F16K 31/122* | (2006.01) |
| *F16K 31/124* | (2006.01) |
| *F16K 31/12* | (2006.01) |
| *A61M 16/06* | (2006.01) |
| *A61M 16/08* | (2006.01) |
| *A61M 39/24* | (2006.01) |

(52) U.S. Cl.
CPC ............ *F16K 31/12* (2013.01); *F16K 31/122* (2013.01); *F16K 31/1221* (2013.01); *F16K 31/1245* (2013.01); *A61M 16/06* (2013.01); *A61M 16/0683* (2013.01); *A61M 16/0816* (2013.01); *A61M 2039/246* (2013.01); *A61M 2039/2433* (2013.01); *A61M 2205/42* (2013.01); *Y10T 137/784* (2015.04); *Y10T 137/7843* (2015.04)

(58) Field of Classification Search
CPC .......... Y10T 137/7889; A61M 16/208; A61M 15/0013; A61M 15/0015; A61M 15/0016; A61M 2039/2406; A61M 2039/242; A61M 2039/2433; A61M 2039/244
See application file for complete search history.

(56) References Cited

U.S. PATENT DOCUMENTS

| | | | | |
|---|---|---|---|---|
| 2,663,309 | A | | 12/1953 | Filliung |
| 3,126,029 | A | * | 3/1964 | Englesson ............ F16K 15/144 137/855 |
| 3,129,721 | A | * | 4/1964 | Nealley ................ F16K 15/145 137/516.11 |
| 3,158,176 | A | | 11/1964 | Toland |
| 3,346,001 | A | | 10/1967 | Camp |
| 3,608,676 | A | * | 9/1971 | Wieck ................... F16K 15/145 137/853 |
| 3,882,891 | A | | 5/1975 | Viles et al. |
| 4,254,791 | A | * | 3/1981 | Bron ................... A01G 25/023 239/533.13 |
| 5,419,739 | A | | 5/1995 | Lewis |
| 5,921,273 | A | | 7/1999 | Ono et al. |
| 6,883,518 | B2 | | 4/2005 | Mittelstadt et al. |
| 8,439,035 | B2 | | 5/2013 | Dantanarayana et al. |
| 10,272,223 | B2 | * | 4/2019 | Hallett ................ A61M 16/206 |
| 2002/0092527 | A1 | * | 7/2002 | Wood ................ A61M 16/1045 128/207.18 |
| 2004/0094157 | A1 | * | 5/2004 | Dantanarayana .......................... A61M 16/0875 128/206.21 |
| 2005/0039757 | A1 | | 2/2005 | Wood |
| 2012/0091381 | A1 | * | 4/2012 | Kern .................... F16K 15/145 251/336 |
| 2013/0160766 | A1 | | 6/2013 | Malouf et al. |
| 2015/0136137 | A1 | | 5/2015 | Dugamelli et al. |
| 2015/0151071 | A1 | * | 6/2015 | Von Moger ....... A61M 16/0666 128/202.27 |

FOREIGN PATENT DOCUMENTS

| | | | | |
|---|---|---|---|---|
| WO | WO 1998/036797 A1 | | 8/1998 | |
| WO | WO-0038772 A1 | * | 7/2000 | ........ A61M 16/0825 |
| WO | WO 0038772 A1 | | 7/2000 | |
| WO | WO 2007/075090 | | 7/2007 | |
| WO | WO 2012/031315 | | 3/2012 | |
| WO | WO 2013/067592 A1 | | 5/2013 | |

OTHER PUBLICATIONS

International Search Report; PCT/NZ2014/000203; dated Dec. 9, 2014; 4 pages.

EPO Extended Search Report; PCT/NZ2014/000203; dated Feb. 6, 2017; 7 pages.

Extended European Search Report for corresponding Application No. 19161103.7 dated Jun. 12, 2019 (6 pages).

* cited by examiner

VALVE WITH INTERNAL MEMBER

CROSS-REFERENCE TO RELATED APPLICATIONS

This application is a continuation application of U.S. application Ser. No. 16/245,118, which has a 371(c) date of Jan. 10, 2019, which is a continuation application of U.S. application Ser. No. 15/022,500, which has a 371(c) date of Mar. 16, 2016, which is a national stage application of International Patent Application No. PCT/NZ2014/000203, filed on Sep. 17, 2014, which claims the benefit of U.S. Provisional Application No. 61/879,012, filed on Sep. 17, 2013 and U.S. Provisional Application No. 61/912,390 filed on Dec. 5, 2013, the entireties of each of which are hereby incorporated by reference.

BACKGROUND OF THE INVENTION

Field of the Invention

The present disclosure generally relates to positive airway pressure therapy. More particularly, the present disclosure relates to valves (e.g., anti-asphyxia valves, constant flow valves) for use in positive airway pressure therapy.

Description of the Related Art

Respiratory disorders deal with the inability of a sufferer to effect a sufficient exchange of gases with the environment, leading to an imbalance of gases in the sufferer. These disorders can arise as a pathological consequence of an obstruction of the airway, insufficiency of the lungs in generating negative pressure, an irregularity in the nervous function of the brain stem, or some other disorder. Treatment of such disorders is diverse and depends on the particular respiratory disorder being targeted. In the first instance, a constriction of the airway, otherwise known as an obstructive apnea or a hypopnea (collectively referred to as obstructive sleep apnea or OSA), can occur when the muscles that normally keep the airway open in a patient relax during slumber to the extent that the airway is constrained or completely closed off, a phenomenon often manifesting itself in the form of snoring. When this occurs for a significant period of time, the patient's brain typically recognizes the threat of hypoxia and partially wakes the patient in order to open the airway so that normal breathing may resume. The patient may be unaware of these occurrences, which may occur as many as several hundred times per session of sleep. This partial awakening may significantly reduce the quality of the patient's sleep, over time potentially leading to a variety of symptoms, including chronic fatigue, elevated heart rate, elevated blood pressure, weight gain, headaches, irritability, depression, and anxiety.

Obstructive sleep apnea is commonly treated with the application of continuous positive airway pressure (CPAP) therapy. Continuous positive airway pressure therapy involves delivering a flow of gas to a patient at a therapeutic pressure above atmospheric pressure that will reduce the frequency and/or duration of apneas and/or hypopneas. This therapy is typically delivered by using a continuous positive airway pressure device (CPAP device) to propel a pressurized stream of air through a conduit to a patient through an interface or mask located on the face of the patient. The stream of air may be heated to near-body temperature. In some configurations, the stream of air may be humidified. In some such configurations, the stream of air may be humidified by forcing the stream of air to travel through a humidification chamber containing water and a heater for heating the water. In such configurations, the heater encourages the evaporation of the water, which in turn partially or fully saturates the stream of air with moisture. This moisture may help to ameliorate discomfort and/or mucosal tissue damage that may arise from the use of unhumidified CPAP therapy.

During exhalation, the patient's exhaled gases typically flow out of bias flow holes located on the interface, on the connection between the interface and the conduit, or elsewhere in the CPAP circuit (where 'circuit' here is defined as the passageway extending from the inlet of the blower to the interface outlet on or within the interface). Such holes are typically made relatively small to reduce noise, and in use the exhaled gases are pushed through the ports or holes by the gases incoming at therapeutic pressure at rates sufficient to keep CO2 rebreathing at acceptable levels. However, under relatively low pressure conditions, for example, when the patient is not receiving therapy, gases exhaled by the patient may not be able escape from such holes at such rates, and additionally a larger volume of exhaled gases may become entrained in the CPAP circuit on the way out to the flow generator/blower inlet. The combination of these two problems may elevate CO2 rebreathing by the patient to unacceptable or undesirable levels.

SUMMARY OF THE INVENTION

In the present disclosure, valves are provided that can be placed in the CPAP circuit that comprises ports open to the environment, where the valve has some means of closing the ports under relatively high pressure conditions (i.e., therapeutic CPAP conditions) and some means of opening the ports under relatively low pressure conditions. In some applications, such valves may be called anti-asphyxia valves (AA valves). In some preferred configurations, such valves are placed close to the patient, e.g. in, at, or close to the interface.

In some configurations, such a valve comprises one or more relatively large ports open to the environment and a flap cantilevered to an internal wall of the valve at one end, where the flap is biased towards a neutral position. Under relatively high pressure conditions, the flap flexes in the direction of the flow and over the ports, and under relatively low pressure conditions, the valve remains in a neutral position (or may flex away from the patient due to exhaled gases flow). In this way, under low pressure conditions, exhaled gases may escape through the ports and the risk of unacceptable CO2 rebreathing may drop to acceptable levels, while under high pressure conditions a low level of leak is maintained and exhaled gases can escape through the bias flow holes.

There are certain disadvantages to such flap-type valves. In these valves, during the transition from a relatively low pressure to a relatively high pressure, the flap quickly 'slaps' or moves over the valve ports in such a way that creates a pressure 'spike' or quick change in pressure in the CPAP circuit, and this 'spike' creates audible noise. Additionally, in such a valve, the flap and the ports are disposed adjacent to each other along the length of the valve, which can make the valve relatively long. In use, a relatively long valve attached to, for example, an interface, may press against a patient's mattress or pillow and displace the mask away from the face, which may disrupt the sealing of the mask. Finally, the traditional port(s) on such a valve is/are relatively large, and exhaled flow through the port(s) may generate a relatively high level of noise due to port size.

Accordingly, it is an object of the invention to present a solution or ameliorate at least one or more of the above problems, or at least provide the public with a useful choice.

The present disclosure also describes valves that can be used as constant flow valves, which are valves that can be used to maintain a constant gas flow rate through a gas conduit under varying pressure conditions. The constant flow valve can progressively close the ports as the flow rate decreases, such that the valve allows relatively more gases to escape to the environment at a higher flow rate and relatively less gases to escape at a lower flow rate. In this way, the flow rate of the gases reaching the mask can be maintained at a generally constant flow rate.

Thus, in accordance with at least one of the embodiments disclosed herein, a valve can comprise a body with an interior surface defining a passageway. One or more ports can extend through the body to provide fluid communication between the passageway and the environment. At least one internal member can be attached to the body at two or more discontinuous attachment positions on the internal member, the internal member having a closed configuration that occludes the one or more ports when a gas pressure in the valve is above a threshold pressure and an open configuration that allows gas to pass from the passageway to the environment when the gas pressure in the valve is at or below a threshold pressure.

In some configurations, the interior surface can be curved.

In some configurations, the at least one internal member can move in a direction that is substantially perpendicular to the direction of gases flow through the valve. The at least one internal member can be configured to progressively roll over the interior surface of the body. The at least one internal member can transition between the open configuration and the closed configuration at a distinct threshold pressure.

The at least one internal member can transition between the open configuration and the closed configuration during a range of pressures. In some configurations, the range of pressures is at least approximately 2 cm H2O and/or less than or equal to approximately 3 cm H2O. In some configurations, the range of pressures is at least approximately 1.5 cm H2O and/or less than or equal to approximately 4 cm H2O.

The one or more ports can be located at generally the same position along the length of the valve as the at least one internal member.

In some configurations, the body can be a round or oval tube and the at least one internal member can extend around at least part of an inner circumference of the body in the closed configuration.

The one or more ports can be disposed around part of the circumference of the body. In some configurations, the one or more ports can be disposed around the entire circumference of the body. The one or more ports can be circular holes having a diameter of approximately 1 mm. In some configurations, the one or more ports have a combined venting area of at least approximately 30 mm$^2$ and/or less than or equal to approximately 600 mm$^2$. In some configurations, the one or more ports have a combined venting area of approximately 40 mm2.

In some configurations, the threshold pressure can be approximately 2 cm H2O.

The length of the at least one internal member between attachment positions can be approximately the same as the length of the interior surface of the body between the attachment positions. In some configurations, the at least one internal member is a continuous member configured to extend around the interior surface of the body in the closed configuration.

The valve can be configured to be placed at an inlet of a patient interface. In some configurations, the valve can be configured to be placed in-line between a patient interface and a blower.

The at least one internal member can be attached to the body by posts that extend through the body. In some configurations, the at least one internal member can be attached to the body by an adhesive. In some configurations, the at least one internal member is attached by overmoulding onto the body.

In some configurations, the valve can be an anti-asphyxia valve. In other configurations, the valve can be a constant flow valve. The at least one internal member can transition between the open configuration and the closed configuration during pressures ranging from at least approximately 0 cm H2O and/or less than or equal to approximately 20 cm H2O.

In accordance with at least one of the embodiments disclosed herein, a valve can comprise a body with an interior surface defining a passageway, the body configured to be positioned in-line with a flow of respiratory gases. One or more ports can extend through the body to provide fluid communication between the passageway and the environment, the one or more ports disposed around at least part of a circumference of the body. At least one internal member can be attached to the body at two or more discontinuous attachment positions on the internal member, the attachment positions being generally at the same location along the length of the valve as the one or more ports. The at least one internal member can be in an open configuration that allows gas to pass from the passageway to the environment when the gas pressure in the valve is at or below a threshold pressure, the at least one internal member being biased radially inward away from the interior surface. Also, the at least one internal member can be in a closed configuration that occludes the one or more ports when a gas pressure in the valve is above a threshold pressure, the at least one internal member moving radially outward toward the interior surface to occlude the one or more ports.

In some configurations, the interior surface can be curved. In some configurations, the body can be round.

In some configurations, the at least one internal member can move in a direction that is substantially perpendicular to the direction of gases flow through the valve. The at least one internal member can be configured to progressively roll over the interior surface of the body. The at least one internal member can transition between the open configuration and the closed configuration at a distinct threshold pressure.

The at least one internal member can transition between the open configuration and the closed configuration during a range of pressures. In some configurations, the range of pressures is at least approximately 2 cm H2O and/or less than or equal to approximately 3 cm H2O. In some configurations, the range of pressures is at least approximately 1.5 cm H2O and/or less than or equal to approximately 4 cm H2O.

In some configurations, the one or more ports can be disposed around the entire circumference of the body. The one or more ports can be circular holes having a diameter of approximately 1 mm. In some configurations, the one or more ports have a combined venting area of at least approximately 30 mm$^2$ and/or less than or equal to approximately 600 mm$^2$. In some configurations, the one or more ports have a combined venting area of approximately 40 mm2.

In some configurations, the threshold pressure can be approximately 2 cm H2O.

The length of the at least one internal member between attachment positions can be approximately the same as the length of the interior surface of the body between the attachment positions. In some configurations, the at least one internal member is a continuous member configured to extend around the interior surface of the body in the closed configuration.

The valve can be configured to be placed at an inlet of a patient interface. In some configurations, the valve can be configured to be placed in-line between a patient interface and a blower.

The at least one internal member can be attached to the body by posts that extend through the body. In some configurations, the at least one internal member can be attached to the body by an adhesive. In some configurations, the at least one internal member is attached by overmoulding onto the body.

In some configurations, the valve can be an anti-asphyxia valve. In other configurations, the valve can be a constant flow valve. The at least one internal member can transition between the open configuration and the closed configuration during pressures ranging from at least approximately 0 cm H2O and/or less than or equal to approximately 20 cm H2O.

BRIEF DESCRIPTION OF THE DRAWINGS

Specific embodiments and modifications thereof will become apparent to those skilled in the art from the detailed description herein having reference to the figures that follow, of which.

DETAILED DESCRIPTION OF SPECIFIC EMBODIMENTS

In the present disclosure, valves are provided that can be placed in-line in the CPAP circuit with ports that are open to the environment, where the valve can close the ports under relatively high pressure conditions and open the ports under relatively low pressure conditions. In some configurations, these types of valves are known as anti-asphyxia vales (AA valves). In some configurations, the valves are placed close to the patient, e.g. in, at, or close to the interface.

In some configurations, the valve comprises one or more relatively large ports open to the environment and a flap cantilevered at one end to an internal wall of the valve, where the flap is biased towards a neutral position. Under relatively high pressure conditions, the flap can flex in the direction of the gases flow and occlude the ports. Under relatively low pressure conditions, the valve can remain in a neutral position (or may flex away from the patient due to exhaled gases flow). Under low pressure conditions, exhaled gases can escape through the ports and the risk of unacceptable CO2 rebreathing may be mitigated to acceptable levels, while under high pressure conditions the venting of exhaled gases is maintained through the bias flow holes.

The present disclosure also describes valves that can be used as constant flow valves, which are valves that can be used to maintain a constant gas flow rate through a gas conduit under varying pressure conditions. For example, as described in further detail below, the constant flow valve can progressively close the ports as the flow rate decreases, such that the valve allows relatively more gases to escape to the environment at a higher flow rate and relatively less gases to escape at a lower flow rate. In this way, the flow rate of the gases reaching the mask can be maintained at a generally constant flow rate.

Figure 1:
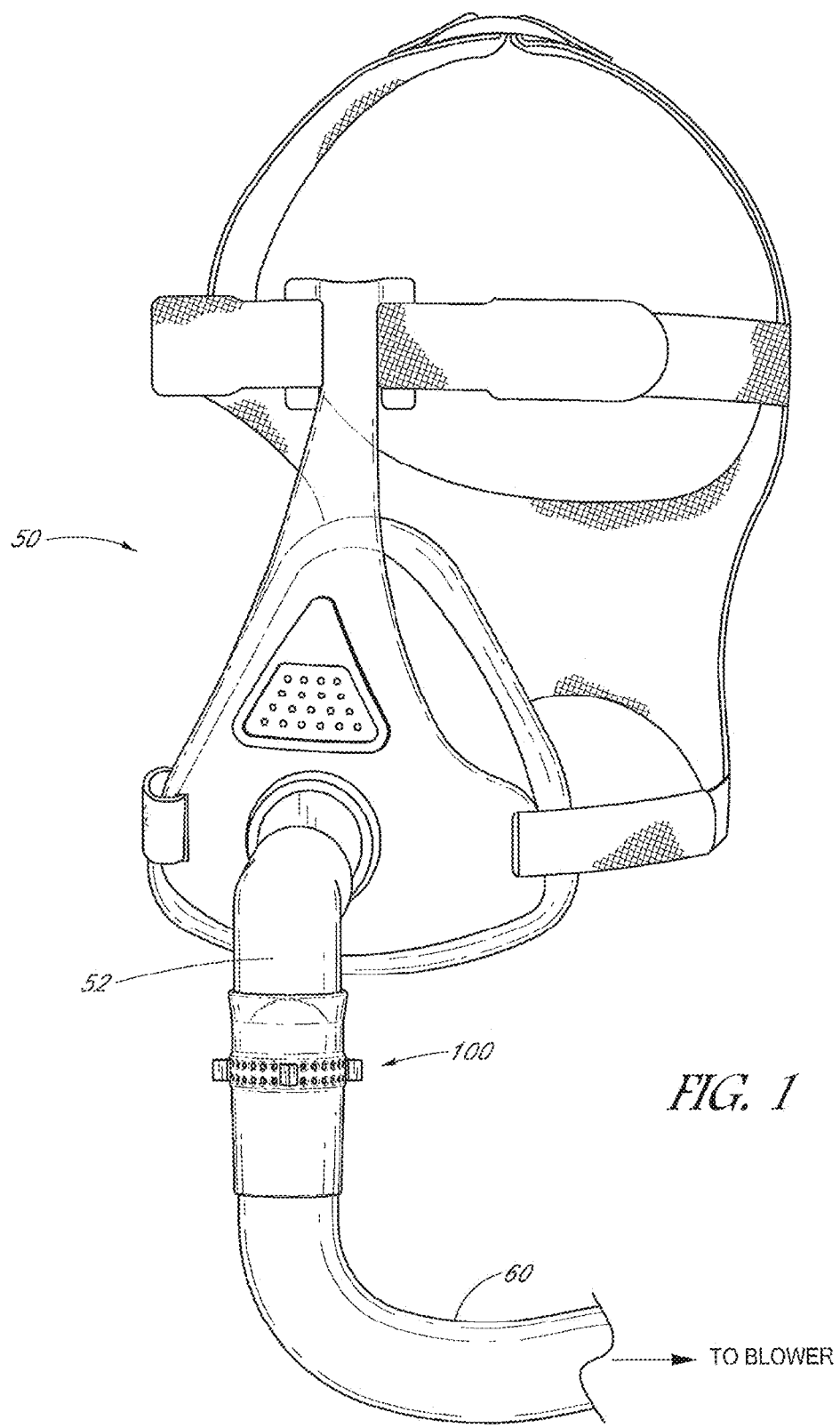
FIG. 1 is a perspective view of an interface with an attached valve in accordance with an embodiment of the present disclosure.

Some non-limiting configurations of valves 100 are illustrated in FIGS. 1-4. FIG. 1 illustrates a valve 100 attached to the elbow connector 52 of a full face mask 50. However, in some embodiments, the valve 100 can be used with any type of patient interface, such as pillow masks, oral masks, oral-nasal masks, nasal masks, nasal cannulae, etc. In the illustrated configuration, the valve 100 is disposed in-line with the gases conduit 60, such that the valve 100 has a first end that is in fluid communication with the mask 50 and a second end that is in fluid communication with the gases conduit 60. The valve can be placed anywhere in the gas circuit between the blower inlet and the interface inlet. However, the valve 100 is preferably attached at or near the inlet of a patient interface.

Positioning the valve closer to the interface inlet beneficially reduces the amount of dead space where $CO_2$ gases can accumulate and beneficially reduces the rebreathing of exhaled gases by the patient. For example, if the valve is positioned near the blower, then CO2 gases would be able to accumulate in at least the mask, elbow connector and the conduit before it can exit to the environment through the valve. The amount of CO2 rebreathing may be at unacceptable levels in this situation. By positioning the valve adjacent the elbow connector, CO2 gases would only accumulate in the mask and elbow connector, reducing the amount of CO2 rebreathing to acceptable levels.

Figure 2:
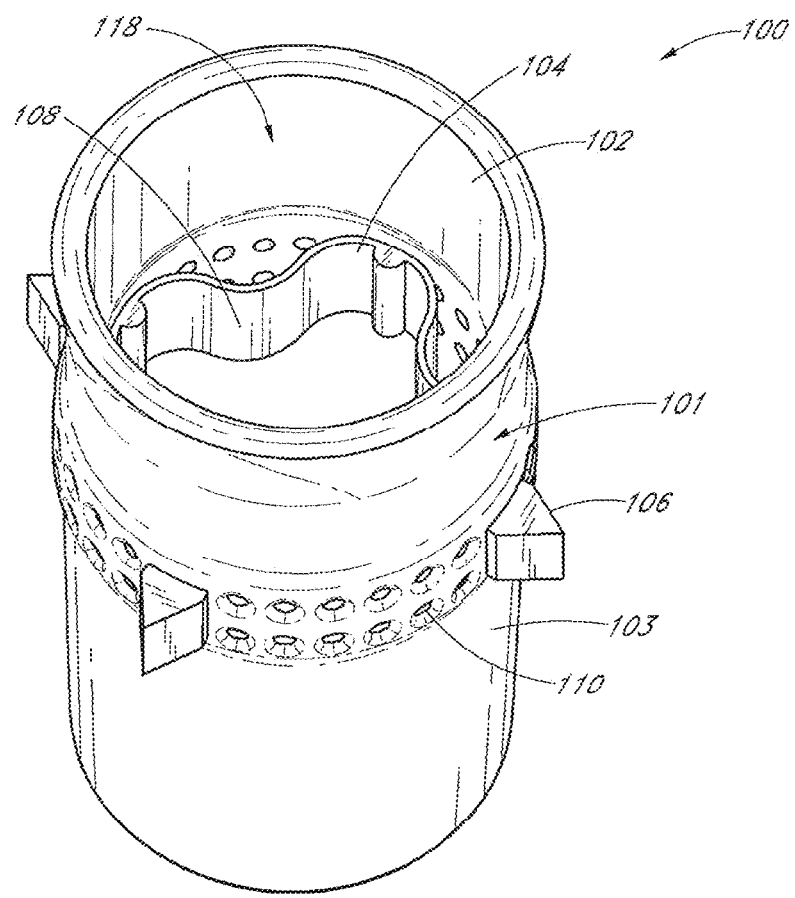
FIG. 2 is a top perspective view of a valve in accordance with an embodiment of the present disclosure.

With reference to FIG. 2, the valve 100 can have a tubular body 101 with an interior surface 102 and an exterior surface 103. The interior surface 102 surrounds a passageway 118 through which fluids can flow. In the illustrated configuration, the valve 100 has a cylindrical shape with a generally circular cross-section. The valve can have any of a plurality of different shapes, such as a tube with an oval, square, rectangular or polygonal cross-section. The internal diameter of the valve can be any size that is suitable for use in a respiratory circuit, preferably without restricting the gas flow. For example, the internal diameter of the body 101 can be approximately 20 mm. In some configurations, the internal diameter of the body can range from at least approximately 15 mm and/or less than or equal to approximately 25 mm.

In some configurations, the body of the valve may not be straight and instead may have a bend, such as a 45 degree or 90 degree bend. The bend in the body of the valve can advantageously help route the circuit to minimize interference with other objects, such as the patient's mattress or pillow, which can lead to displacement of the mask away from the face and disruption of the mask seal. In some configurations, the valve can be integrated or built into the elbow connector. This can position the valve closer to the interface inlet, beneficially reducing the amount of dead space, as discussed above.

Figure 3:
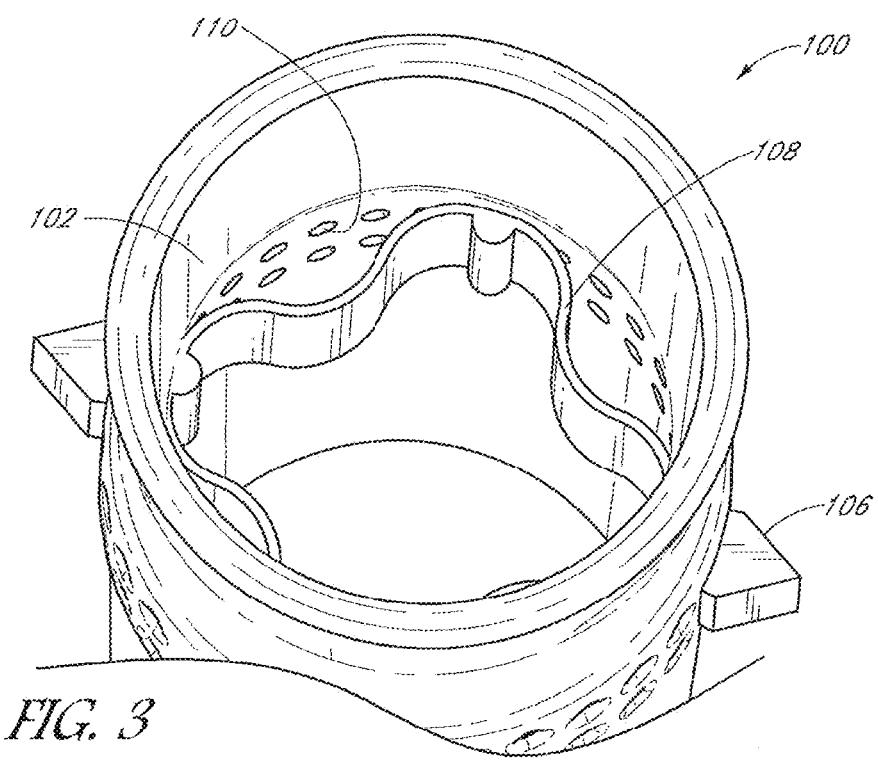
FIG. 3 is close-up view of the valve of FIG. 2.
Figure 4:
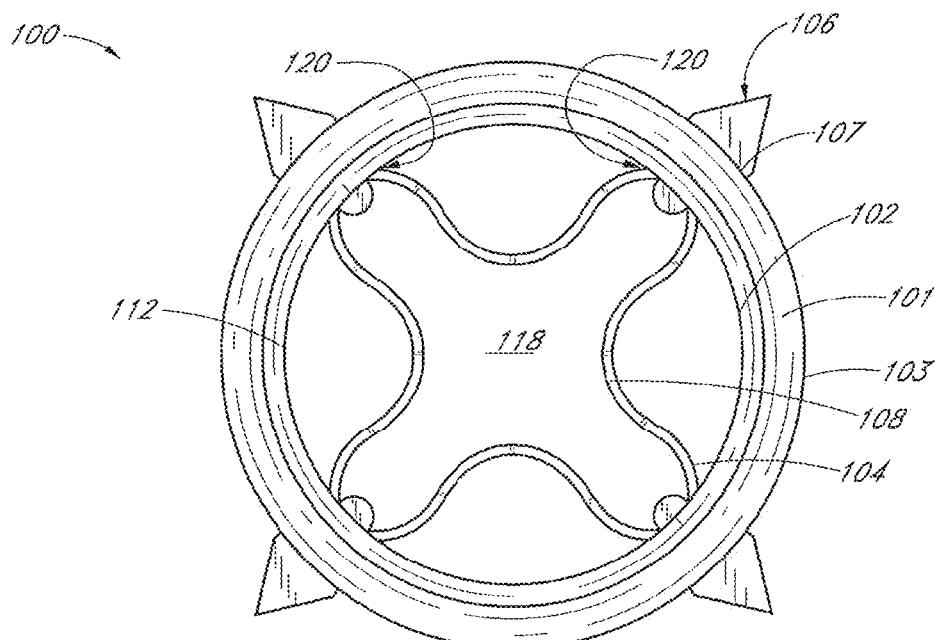
FIG. 4 is a top plan view of the valve of FIG. 2.

The valve 100 has an internal member 104 that can be coupled to the interior wall 102 of the valve 100, as illustrated in FIGS. 2-4. The internal member can be configured to occlude the ports of the valve when the gas flow pressure is above a threshold pressure and not occlude the ports when the gas flow pressure is below the threshold pressure, as described in further detail below. In the illustrated configuration, the internal member 104 is an elongate ribbon in the passageway 118 that is apposed to the ports of the valve 100. The illustrated internal member 104 is a continuous ribbon that is attached to the body 101 by three posts 106 that extend through the body 101 of the valve 100.

With continued reference to FIG. 2, the valve 100 comprises one or more ports 110. The ports 110 can be through holes in the body 101 of the valve 100 that extend from the interior surface 102 to the exterior surface 103 such that the passageway 118 is in fluid communication with the environment through the ports 110. In the illustrated configuration, the valve 100 has a plurality of relatively small ports 110 that are arranged in two rows extending around the body 101. The ports 110 are located at approximately the same position along the length of the valve 100 as the internal member 104, such that the internal member 104 can overlap and occlude the ports 110 when the gas flow pressure is above a threshold pressure.

When the gas flow pressure is below a certain threshold, the internal member 104 is in its neutral configuration and curves away from the interior surface 102, forming folds 108 in the internal member 104. The folds 108 are approximately the same length as the sealing surface 112, which is the area on the interior wall 102 between the posts 106 where the ports 110 are disposed. When the gas flow pressure is above a certain threshold, the folds 108 are urged to curve toward the interior surface 102 until the folds 108 of the internal member 104 abut the sealing surface 112 and occlude the ports 110.

Figure 5:
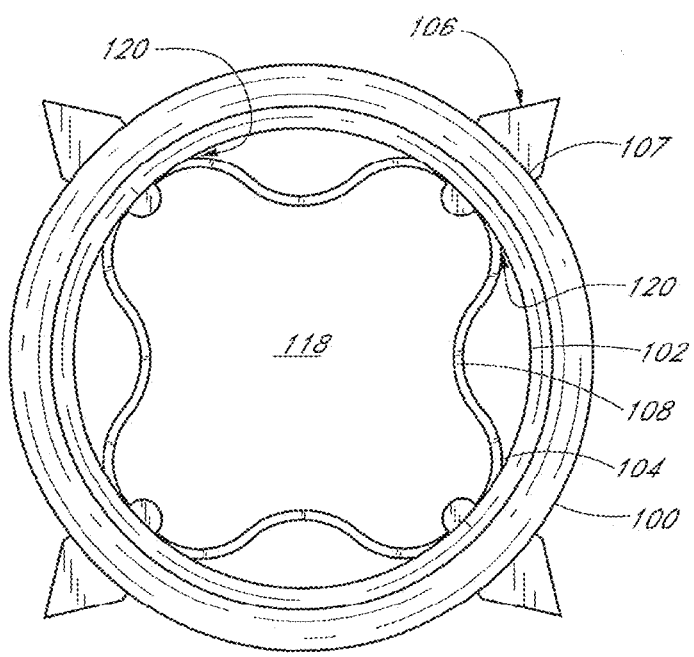
FIG. 5 is a top plan view of the valve of FIG. 2 in a partially closed configuration.

In use, under relatively low pressure conditions, exhaled gases can escape through ports 110 when the internal member 104 is in a neutral position as shown in FIG. 4. In the neutral position, the internal member 104 does not occlude the ports 110 and exhaled gases can flow freely through the ports 110 to the environment. When the system transitions to relatively high pressure conditions (e.g. the CPAP blower is turned on) and the pressure of the gas flow meets or exceeds a threshold pressure, the leading contact edges 120 of the folds 108 of the internal member 104 can roll to abut the sealing surface 112 of the valve 100, thereby occluding the ports 110 as shown in FIG. 5. In some configurations, the pressure of the gases moving through the valve 100 can apply forces on the folds 108 of the internal member 104 to move the folds 108 against the interior surface 102 of the valve 100 in a direction substantially perpendicular to the direction of gas flow. In these configurations, the folds 108 are moved substantially by the gas pressure within the valve 100 and not by the forces from the gas velocity, and the valve 100 can be described as a pressure-dependent valve rather than a flow-dependent valve.

The internal member is preferably configured to be flexible. The internal member can be made of a pliable material that can bend and flex easily, such as for example silicone. The internal member can also have a shape that is configured for flexibility, such as for example a thin, flat shape. The thickness of an internal member for an AA valve can be at least approximately 0.3 millimeter and/or less than or equal to approximately 0.4 millimeter. This internal member may have an operating threshold pressure of approximately 2-3 cm H2O. In some configurations, the thickness of the internal member can be at least approximately 0.1 millimeter and/or less than or equal to approximately 0.5 millimeter.

The valves described herein advantageously operate without significantly restricting the flow path. As mentioned above, the internal member 104 moves in a direction substantially perpendicular to the direction of gas flow and only a thin edge, or cross-section, of the internal member 104 is in the path of the gas flow, as can be seen in FIG. 4. In contrast, other valve designs, such as the flap type valve, can restrict the flow path. For example, a flap valve in certain positions may almost completely block the flow path and the air flow is forced to go around the flap valve or push the flap out of the way. This can affect the flow measurements of the respiratory device (e.g., CPAP). The valves disclosed herein advantageously are not flow dependent, rather pressure dependent, and can even operate when there is no change in flow velocity or even zero flow velocity.

Figure 6:
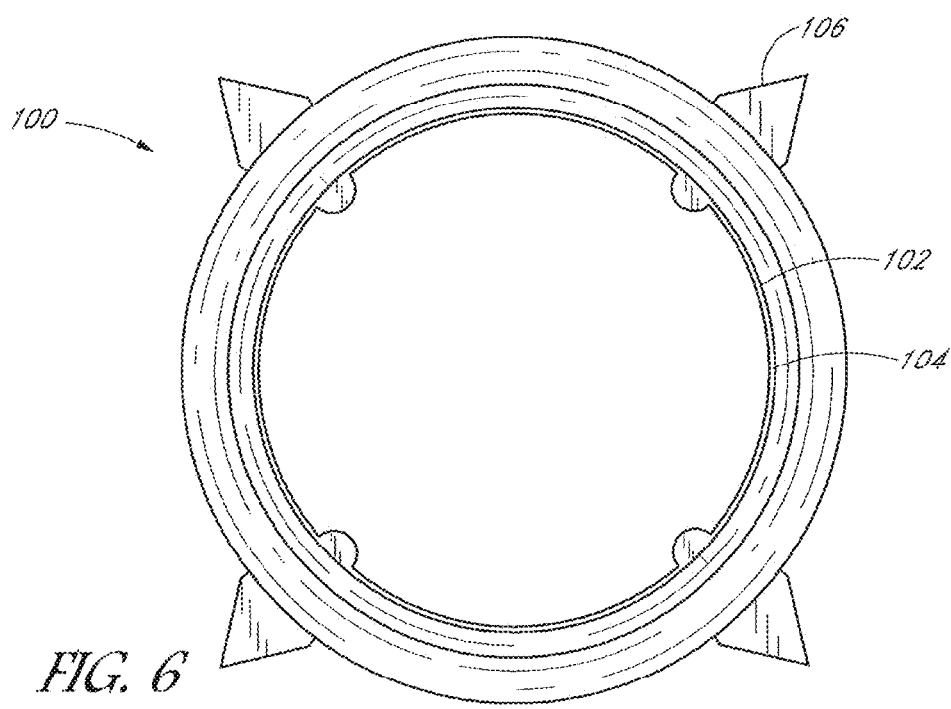
FIG. 6 is a top plan view of the valve of FIG. 2 in an almost fully or fully closed configuration.

In some configurations, the rolling motion of the internal member 104 and the progressive occlusion of the ports 110 can advantageously help to reduce valve noises, which are traditionally caused by the slapping motion of a traditional flap valve. When the internal member 104 is exposed to gas flow that meets or exceeds the threshold pressure, the folds 108 of the internal member 104 can gradually roll over the sealing surface 112 until the sealing surface 112 and the ports 110 are substantially covered by the folds 108 and the valve 100 is substantially in a closed configuration, as shown in FIG. 6. FIGS. 4-6 taken together may represent a continuum of internal member 104 positions from substantially open to substantially closed. In some configurations, the pressure at which the valve 100 may close from an open state, or open from a closed state, is approximately 2 cm H2O. In some configurations, the pressure at which the valve transitions from the open and closed states can be at least approximately 2 cm H2O and/or less than or equal to approximately 3 cm H2O. In some configurations, the pressure at which the valve transitions from the open and closed states can be at least approximately 1.5 cm H2O and/or less than or equal to approximately 4 cm H2O.

In some configurations, the internal member 104 can progressively abut the sealing surface 112 through a range of operating pressures. For example, the internal member 104 can be in a fully open configuration, as illustrated in FIG. 4, until the gas pressure increases to reach approximately a lower threshold pressure, such as 1.5 cm H2O. The folds 108 can gradually roll to abut an increasing area of the sealing surface 112 as the pressure continues to increase. An increasing number of ports 110 are also progressively occluded as the folds 108 gradually roll against the sealing surface 112. Thus, as the gas pressure increases, the total area of the ports 110 through which exhaled gases can escape decreases. When the gas pressure reaches approximately an upper threshold pressure, such as 4 cm H2O, the folds 108 can be substantially abutted against the sealing surface 112 in a fully closed configuration.

Similarly, as the gas pressure decreases, the internal member 104 can start to gradually roll away from the sealing surface when the gas pressure reaches approximately an upper threshold pressure. The internal member 104 can progressively roll away from the sealing surface 112 as the gas pressure continues to decrease. An increasing number of ports 110 are also progressively opened as the folds 108 gradually roll away from the sealing surface 112, and the total area of the ports 110 increases. When the gas pressure reaches approximately a lower threshold pressure, the folds 108 are substantially separated from the sealing surface, as illustrated in FIG. 4, and the internal member 104 is in a fully open configuration. In some configurations, the lower threshold pressure can be at least approximately 1.5 cm H2O and/or less than or equal to approximately 2.5 cm H2O. In some configurations, the upper threshold pressure can be at least approximately 3 cm H2O and/or less than or equal to approximately 4 cm H2O.

The range of operating pressures of the internal member 104 while transitioning from an open to a closed configuration can be the same as the range of pressures for transitioning from a closed to an open configuration. For example, the internal member 104 can start to roll onto the sealing surface 112 into a closed configuration at approximately 1.5 cm H2O and be in a fully closed configuration at approximately 4 cm H2O. The same internal member 104 can start to roll away from the sealing surface 112 into an open configuration at approximately 4 cm H2O and be in a fully open configuration at approximately 1.5 cm H2O.

In some configurations, the range of operating pressures can be different depending on whether the internal member 104 is transitioning from an open to closed configuration, or from a closed to open configuration. For example, the internal member 104 can start to roll onto the sealing surface 112 into a closed configuration at approximately 2 cm H2O and be in a fully closed configuration at approximately 4 cm H2O. The same internal member 104 can start to roll away from the sealing surface 112 into an open configuration at approximately 3 cm H2O and be in a fully open configuration at approximately 1.5 cm H2O.

In some configurations, the internal member 104 can transition from the open configuration to the closed configuration at a particular threshold pressure, instead of gradually transitioning throughout a range of operating pressures. The valve can act as a "digital valve" where the internal member is in an open configuration when the gas pressure is at or below a threshold value, and in a closed configuration when the gas pressure is above the threshold value. For example, the internal member can be in the fully open configuration until the gas pressure reaches the threshold value, such as 2 cm H2O. When the threshold value is reached, the internal member can transition to the fully closed configuration.

In some configurations, the valve can be a constant flow valve that helps maintain a generally constant gas flow rate through a gas conduit under varying pressure conditions. As described above, the internal member can progressively roll over the ports through a range of pressures. In constant flow valves, the internal member can progressively occlude the ports as the flow rate decreases, which causes the pressure to increase. The valve allows relatively more gases to escape to the environment through the ports at a higher flow rate and relatively less gases to escape at a lower flow rate such that a generally constant flow rate, or at least a small range of flow rates, is delivered to the mask. Preferably, the internal member is thicker compared to the internal member used for some other valves, such as the AA valve. For example, the thickness of the internal member for a constant flow valve can be approximately 0.7 millimeter. In some configurations, the thickness of the internal member for a constant flow valve can range from at least approximately 0.5 millimeter and/or less than or equal to approximately 1.0 millimeter. In some configurations, the internal member can start to roll onto the sealing surface into a closed configuration at approximately 0 cm H2O and be in a fully closed configuration at approximately 20 cm H2O.

In a constant flow valve the internal member can progressively abut the sealing surface through a range of operating flow rates, which inversely corresponds to a range of operating pressures. For example, the internal member can be in a fully open configuration at a relatively high gas flow rate until the gas flow rate decreases to reach approximately an upper threshold flow rate. The upper threshold flow rate can have a corresponding gas pressure, such 0 cm H2O. The folds of the internal member can gradually roll to abut an increasing area of the sealing surface as the flow rate decreases, and consequently causes the pressure to increase. An increasing number of ports are also progressively occluded as the folds gradually roll against the sealing surface. Thus, as the flow rate decreases and the gas pressure increases, the total area of the ports through which gases flowing through the valve can escape to environment decreases, allowing more gases to reach the mask. When the flow rate reaches approximately a lower threshold flow rate, the folds can be substantially abutted against the sealing surface in a fully closed configuration such that substantially all the gases flowing through the constant flow rate valve are delivered to the mask. The lower threshold flow rate can have a corresponding gas pressure, such as 20 cm H2O.

Similarly, as the flow rate increases and the gas pressure decreases, the internal member can start to gradually roll away from the sealing surface at approximately a lower threshold flow rate. The lower threshold flow rate can have a corresponding gas pressure, such 20 cm H2O. The internal member can progressively roll away from the sealing surface as flow rate increases and consequently the gas pressure decreases. An increasing number of ports are also progressively opened as the folds gradually roll away from the sealing surface and the total area of the ports through which gases can escape to the environment increases. When the flow rate reaches approximately an upper threshold flow rate, the folds are substantially separated from the sealing surface and the internal member is in a fully open configuration, such that gases are allowed to escape through all the ports of the valve. The upper threshold flow rate can have a corresponding gas pressure, such as 0 cm H2O.

The illustrated internal member 104 has generally an elongate, rectangular shape. In some configurations, the internal member 104 can have other shapes, such as for example round shapes or zig-zag shapes. The internal member can be made of a pliable material that can bend and flex easily from the open configuration to the closed configuration. For example, the internal member can at least partially be made of silicone, rubber, flexible plastics, paper, etc.

In some configurations, as illustrated in FIGS. 2 and 3, the ports 108 are located at approximately the same position along the length of the valve 100 as the internal member 104, such that the internal member 104 can overlap and occlude the ports 110 when the gas flow pressure is above a threshold pressure. These configurations advantageously provide for a valve 100 that is compact and shorter in length than traditional valves, where the ports and valve flaps are sequentially next to each other along the length of the valve.

In some configurations, as illustrated in FIGS. 2-4, the internal member 104 is attached to the valve 100 by posts 106 that extend through the body 101 of the valve 100. The posts 106 can be made of the same material as the internal member 104. In some configurations, the posts 106 and internal member 104 can be made from different materials. For example, the posts 106 may be made of a plastic material while the internal member 104 is made of rubber. The two components can be welded, adhered or otherwise coupled together. In some configurations, during assembly the posts 106 can be forced through orifices that extend through the valve body 101. The orifices can be similarly-sized to the posts for a close fit between the orifices and posts. The posts 106 can have flanges 107 that are wider than the orifices to hold the posts in place and to help prevent the posts from being pulled back through the orifices, as illustrated in FIG. 4.

The internal member 104 can be coupled to the body 101 by any of a plurality of different types of functional couplers. For example, the internal member 104 can be glued to the interior surface 102 of the valve 100 using an adhesive, overmoulded onto the body 101 of the valve 100, or affixed to the interior surface 102 of the valve 100 via ultrasonic welding. Any suitable attachment method can be used and preferably the internal member 104 is pliable enough to cover the ports 110, in use.

In some configurations, the internal member 104 can be removable from the valve body 101 for easy replacement, cleaning or service. For example, the posts 106 can be deformable so that they can be detached from the body 101 and preferably re-attachable after cleaning or servicing. A removable internal member can advantageously allow for customization of the valve performance, such as customizing the gas pressure at which the internal member switches from the open to closed configuration.

Figure 7:
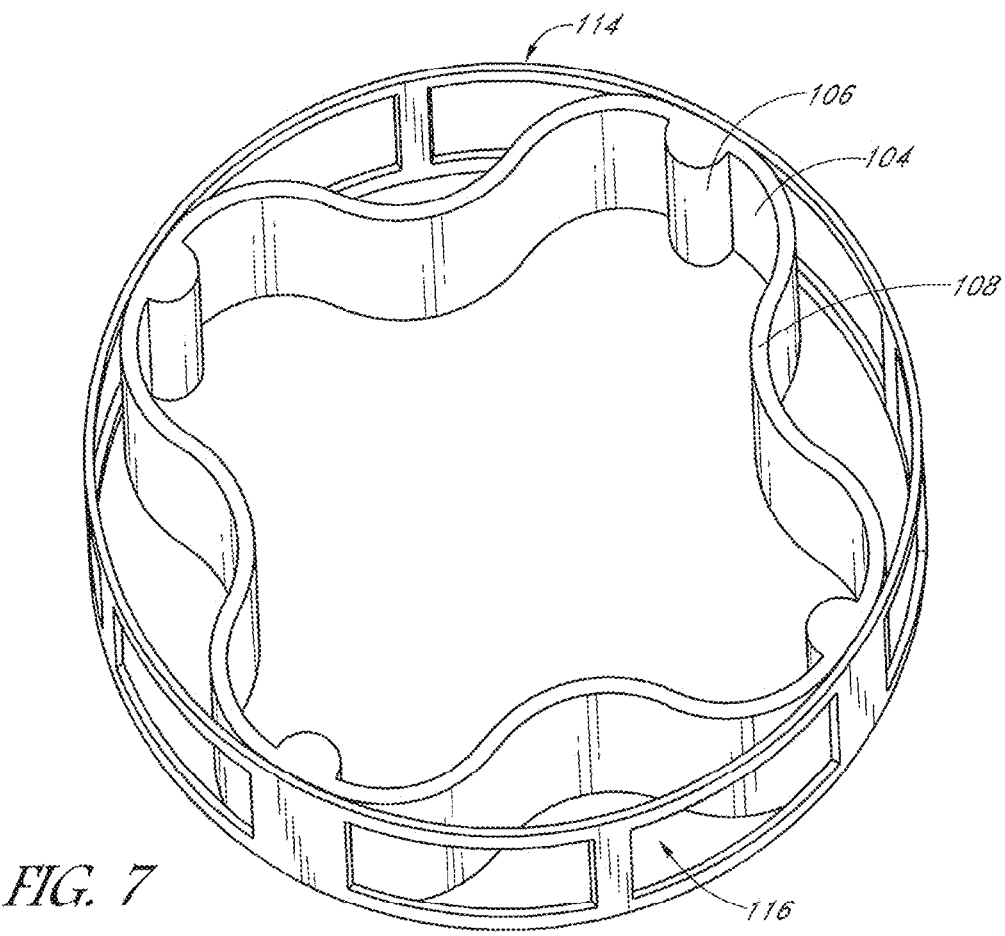
FIG. 7 is a top perspective view of an internal member on an internal ring support in accordance with an embodiment of the present disclosure.
Figure 8:
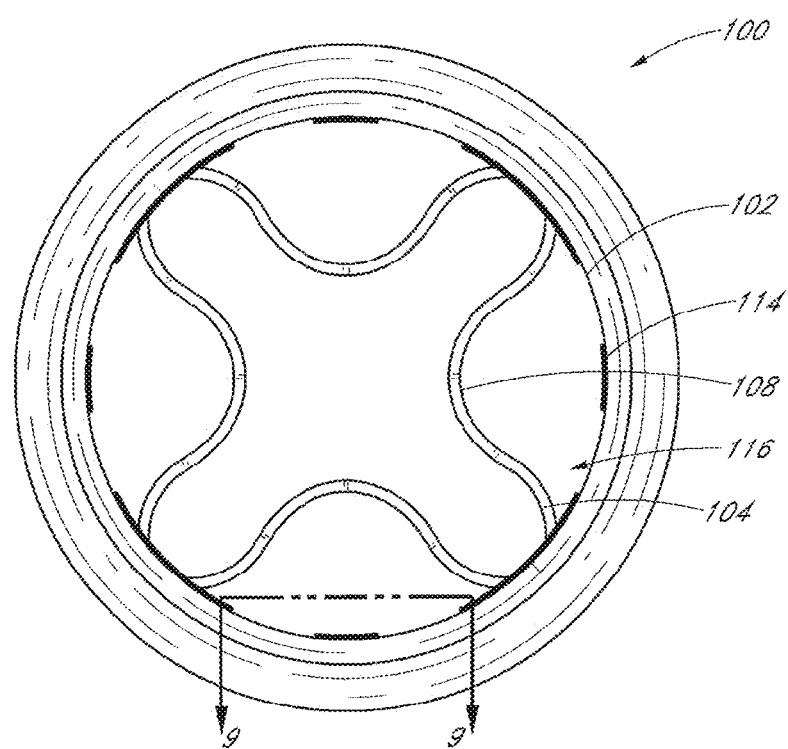
FIG. 8 is a top plan view of a valve with the internal member of FIG. 7.
Figure 9:
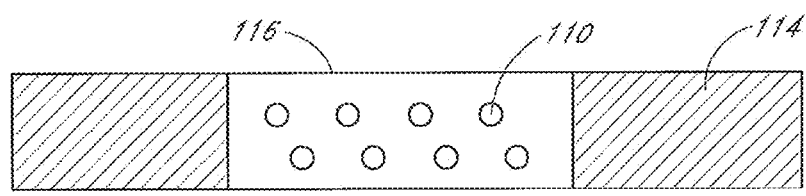
FIG. 9 is a cross-sectional view of the internal ring of FIG. 8.

In some configurations, the internal member 104 can be attached to an internal ring 114 or other element that may be inserted inside the passageway 118 of the valve 100, instead of or in addition to being attached or anchored directly to the body 101 of the valve 100, as illustrated in FIGS. 7-8. With reference to FIGS. 7 and 9, the internal ring 114 can have gaps 116 through which gases can flow through to the ports 110. The internal ring 114 can be pressed into the body 101 of the valve 100, such as through an interference fit, or can be coupled by any retaining feature, such as for example hooks, clips, screw threads, tongue-and-grooves, etc. The internal ring 114 can be removable from the body 101 of the valve 100, and in some configurations, the internal member 104 can be removable from the internal ring 114.

The ports 110 are through holes in the body 101 of the valve 100 that enable fluid communication between the passageway 118 and the environment. The ports 110 can be any suitable size, shape, and/or configuration. In the illustrated configurations, the ports are small circular holes that are generally perpendicular to the body 101, such that the ports extend normal to the interior and exterior surfaces. In other configurations, the ports can extend at an angle to the body 101. The port directions can allow for directing the flow of gases vented from the valve. In some configurations, the ports can have an oval shape, rectangular shape, or other shape besides circular holes. For example, the ports can comprise an elongate oval shaped hole disposed between the posts. In some configurations, the ports can include a combination of different shaped holes, such as polygonal ports and oval ports. The ports are preferably relatively small holes, which can help reduce noises from the venting gases. In some configurations, the ports are substantially circular holes of approximately 1 mm in diameter. In some configurations, the ports can range from at least approximately 0.5 mm in diameter and/or less than or equal to approximately 3 mm in diameter.

The total venting area of the ports is configured to allow adequate CO2 flushing while keeping the ports small to reduce venting noises. For example, the total cross-sectional area of all the ports can be approximately 40 $mm^2$. This can be achieved, for example, with approximately 50 ports, each having a 1 mm diameter hole. In some configurations, the total cross-sectional area of all the ports can range from at least approximately 30 $mm^2$ and/or less than or equal to approximately 600 $mm^2$.

Figure 10:
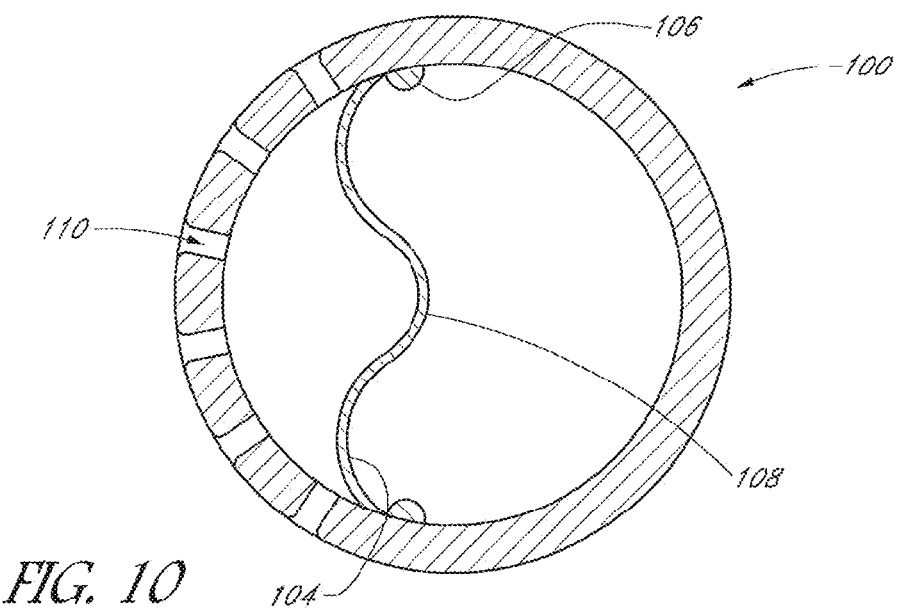
FIG. 10 is a cross-sectional top plan view of an internal member on one side of the valve in accordance with an embodiment of the present disclosure.

With reference to FIGS. 1-3 and as described above, the illustrated embodiment comprises a plurality of ports that are arranged in two rows extending around the body 101. In some configurations, the ports may comprise a plurality of holes arranged in a single row or more than two rows extending around the body, or partially around the body. The ports 110 are located at approximately the same position along the length of the valve 100 as the internal member 104, such that the internal member 104 can overlap and occlude the ports 110 when the gas flow pressure is above a threshold pressure. In some configurations, the ports may only be disposed around a portion or portions of the body. For example, the ports may be disposed on half of the circumference of the body, as illustrated in FIG. 10. In another example, the ports may be disposed on two opposite portions of the body.

In some preferred configurations, the size of the ports 110 is selected in such a way that both acceptable CO2 flushing and acceptable noise generation are achieved. In some preferred configuration, the valve ports 110 and the internal member 104 are coaxial along the length of the valve 100, which may be an efficient use of space.

The length of the folds 108 of the internal member 104 can be approximately the same length as the corresponding sealing surface 112, such that the internal member 104 adequately occludes all the ports 110 when the internal member 104 is in the closed configuration. In some configurations, the folds 108 can be slightly shorter or slightly larger in length than the sealing surface 112 and still provide sufficient occlusion of the ports 110. The internal member 104 can be made of a pliable material, such as rubber, that can stretch and/or compress to conform to the length of the sealing surface 112. For example, in a valve having an internal diameter of about 20 mm, the length of the internal member extending around the entire interior surface can be approximately 61 mm.

Figure 11:
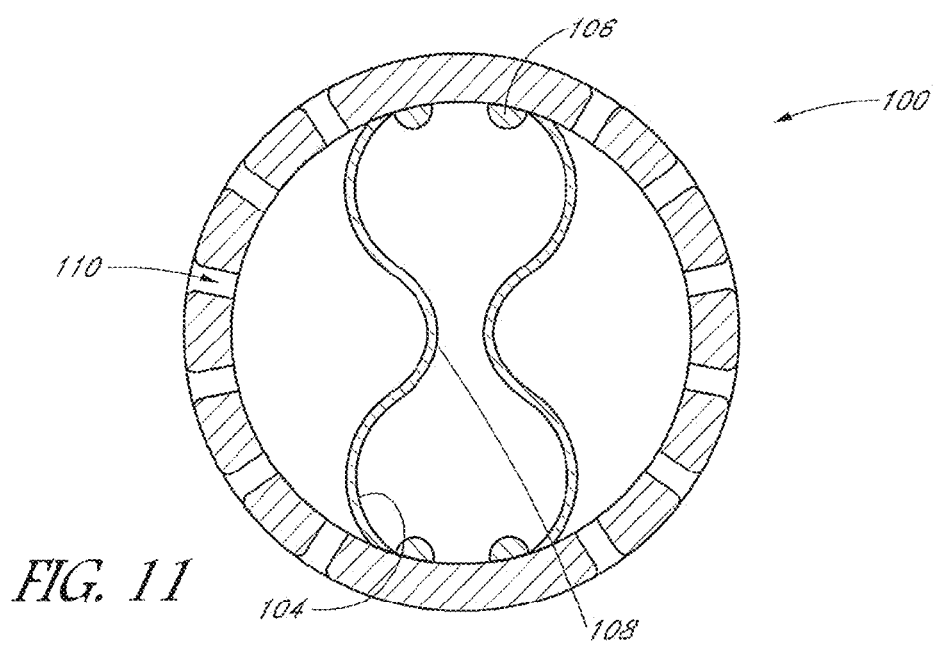
FIG. 11 is a cross-sectional top plan view of a valve with internal members on opposite sides of the valve in accordance with an embodiment of the present disclosure.

In the embodiments illustrated in FIGS. 2-6, the internal member 104 is a single continuous member connected integrally with the posts 106. However, in other embodiments, the internal member 104 can be several discontinuous internal members, each attached to the body 101 at both ends of the internal member, such as illustrated in FIGS. 10-11. FIG. 10 illustrates a cross-sectional view of a valve 100 with an internal member 104 that comprises a single fold 108 and is attached to the interior surface 102 at both ends of the internal member 104. The valve 100 comprises a set of ports 110 on one side of the valve 100. FIG. 11 illustrates a configuration of a valve 100 comprising two internal members 104, each comprising a fold 108. Each internal member 104 is attached to the interior surface 102 at both ends of the internal members 104.

Figure 12:
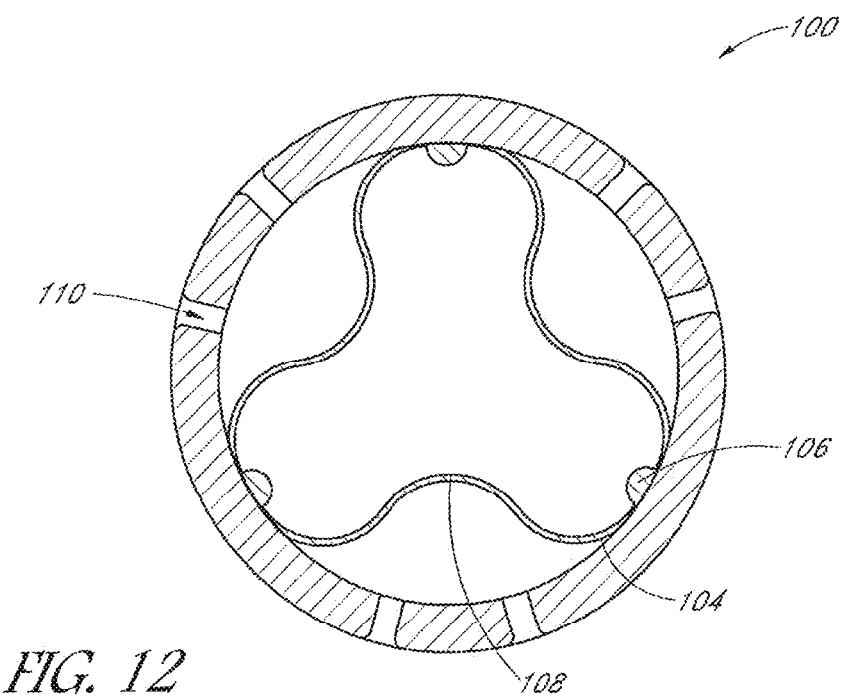
FIG. 12 is a cross-sectional top plan view of a valve with an internal member having four folds in accordance with an embodiment of the present disclosure.
Figure 13:
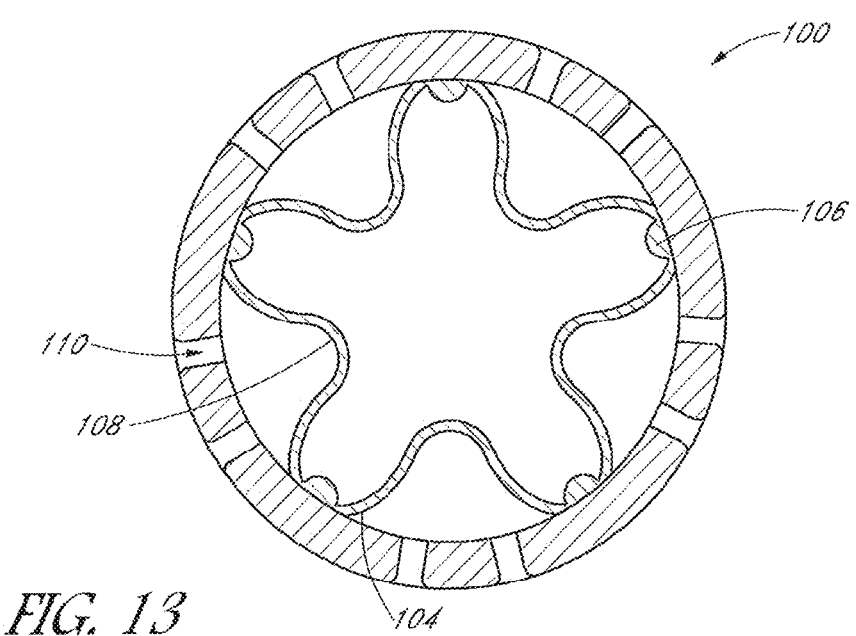
FIG. 13 is a cross-sectional top plan view of a valve with an internal member having five folds in accordance with an embodiment of the present disclosure.

The internal member 104 can have any number of folds 108. For example, the internal member 104 can comprise one, two, three or more than three folds 108 along the length of the internal member 104. Some non-limiting examples of these configurations are shown in FIGS. 12-13. FIG. 12 illustrates a configuration of a valve 100 in which the internal member 104 comprises four folds 108 and the valve 100 comprises four sets of ports 110. FIG. 13 shows a configuration in which the internal member 104 comprises five folds 108 and the valve 100 comprises five sets of ports 110. As implied in FIGS. 10-13, the valve can comprise any number of folds and a corresponding number of sets of ports. However, in some embodiments, the number of folds and the number of sets of port may not be the same.

Figure 17:
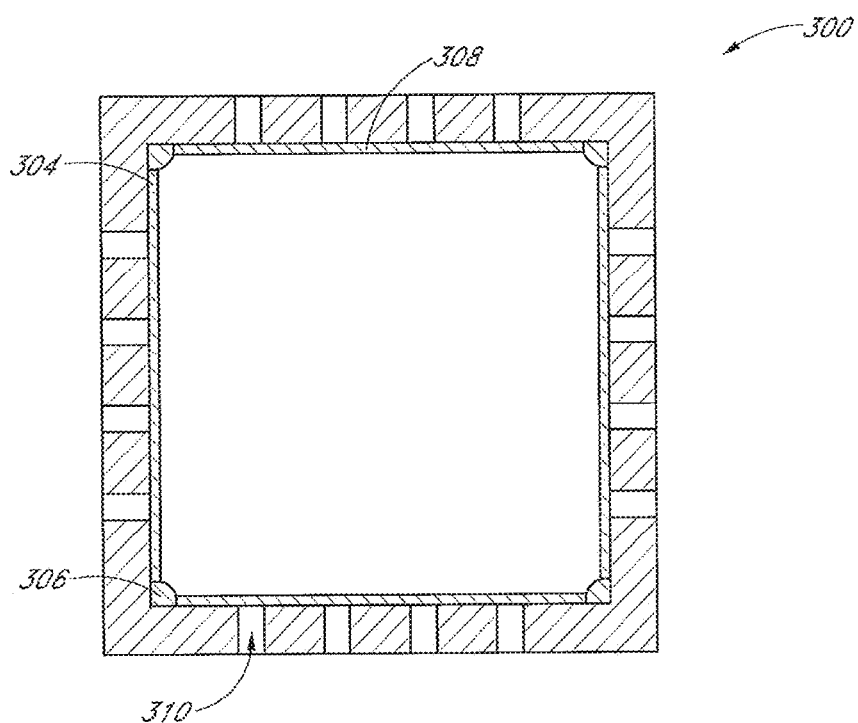
FIG. 17 is a cross-sectional top plan view of the valve of FIG. 16, in the closed configuration.
Figure 18:
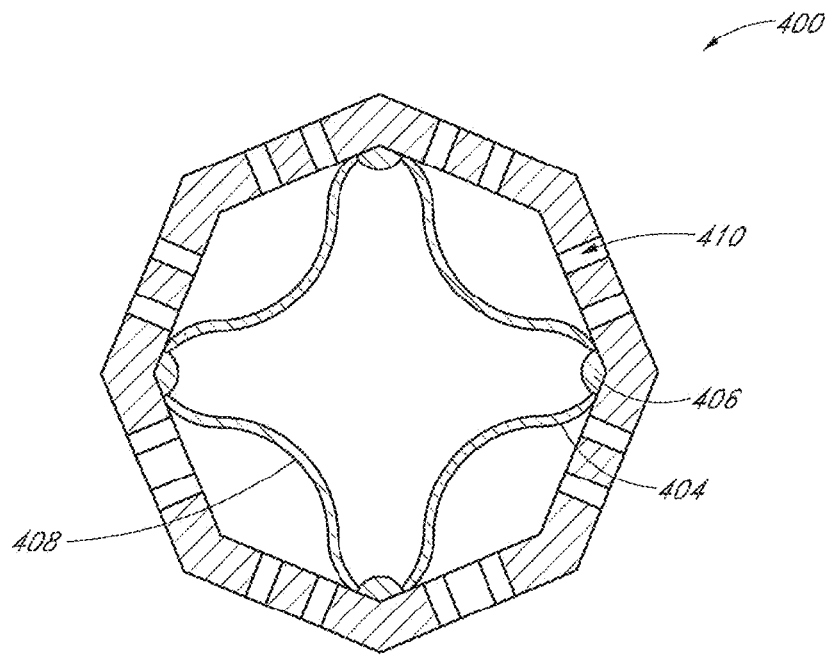
FIG. 18 is a cross-sectional top plan view of a valve with an octagonal shaped body in accordance with an embodiment of the present disclosure.
Figure 19:
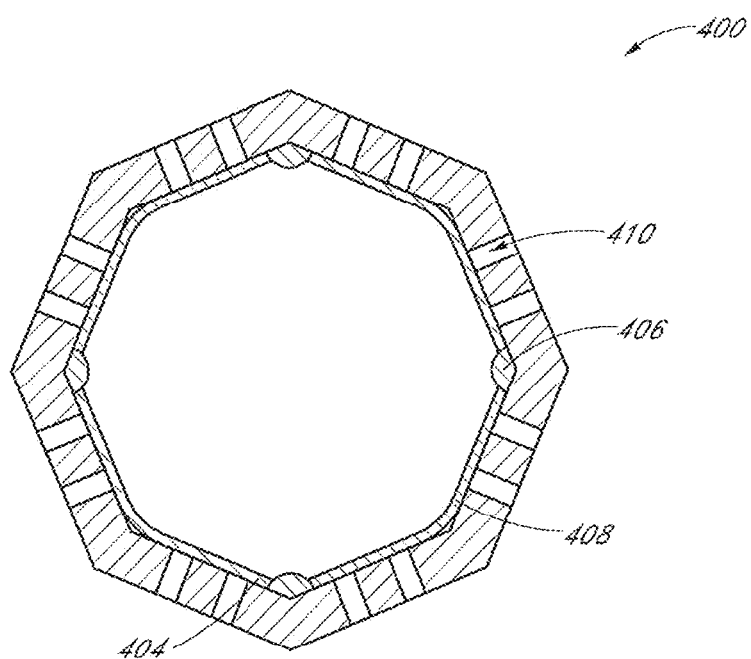
FIG. 19 is a cross-sectional top plan view of the valve of FIG. 18, in the closed configuration.
Figure 20:
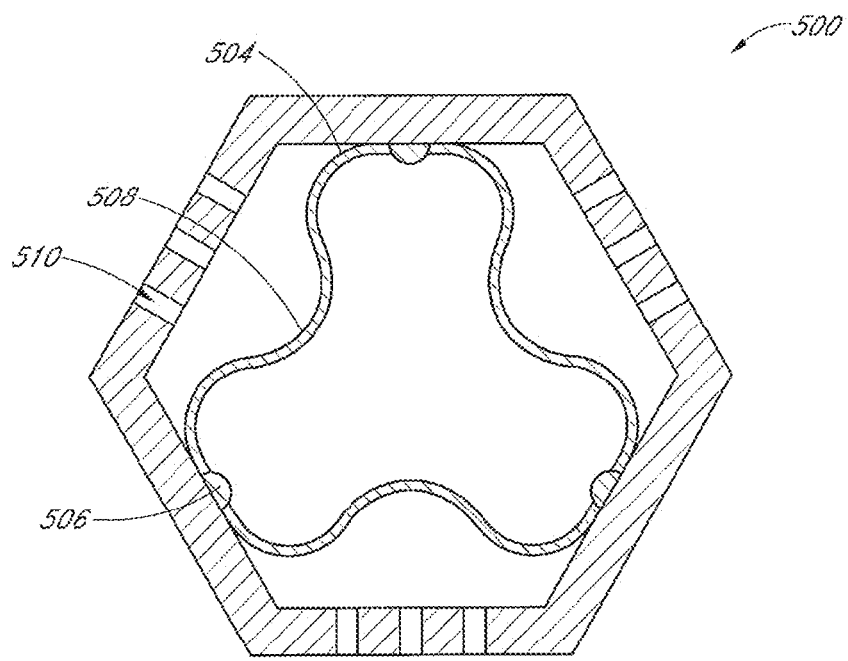
FIG. 20 is a cross-sectional top plan view of a valve with a hexagonal shaped body in accordance with an embodiment of the present disclosure.
Figure 21:
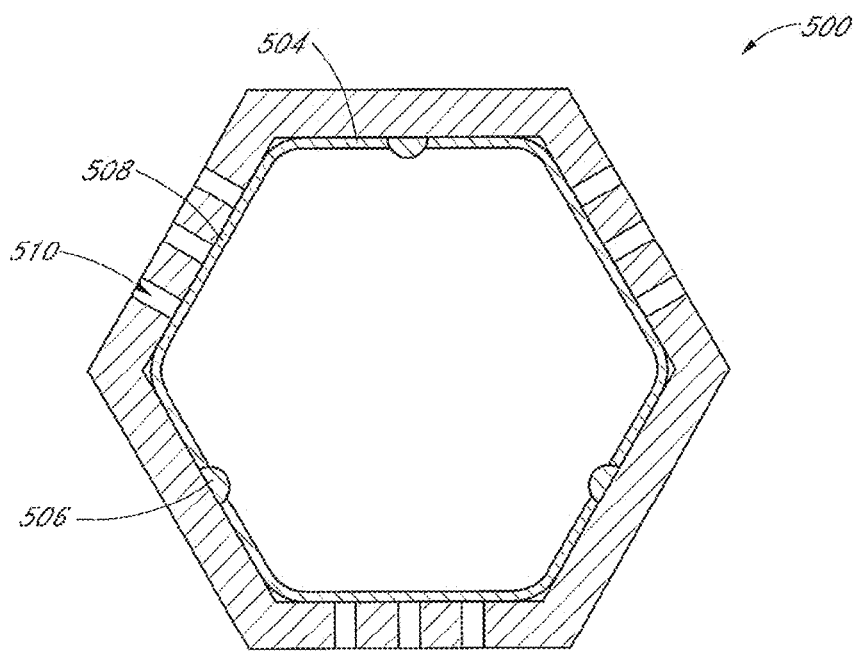
FIG. 21 is a cross-sectional top plan view of the valve of FIG. 20, in the closed configuration.

The valve body can have any of a plurality of different shapes, in addition to the circular or round shapes described above. In some configurations, the valve body can be a tube with a square cross-sectional shape, as illustrated in FIGS. 14-17. The valve body can be a tube having an octagonal cross-sectional shape, as illustrated in FIGS. 18-19, or a hexagonal cross-sectional shape, as illustrated in FIGS. 20-21. In some configurations, the valve body can be a tube with other cross-sectional shapes besides those provided in the examples of FIGS. 14-21, such as rectangular, oval, triangular, other polygonal shapes, or any other shape.

Figure 14:
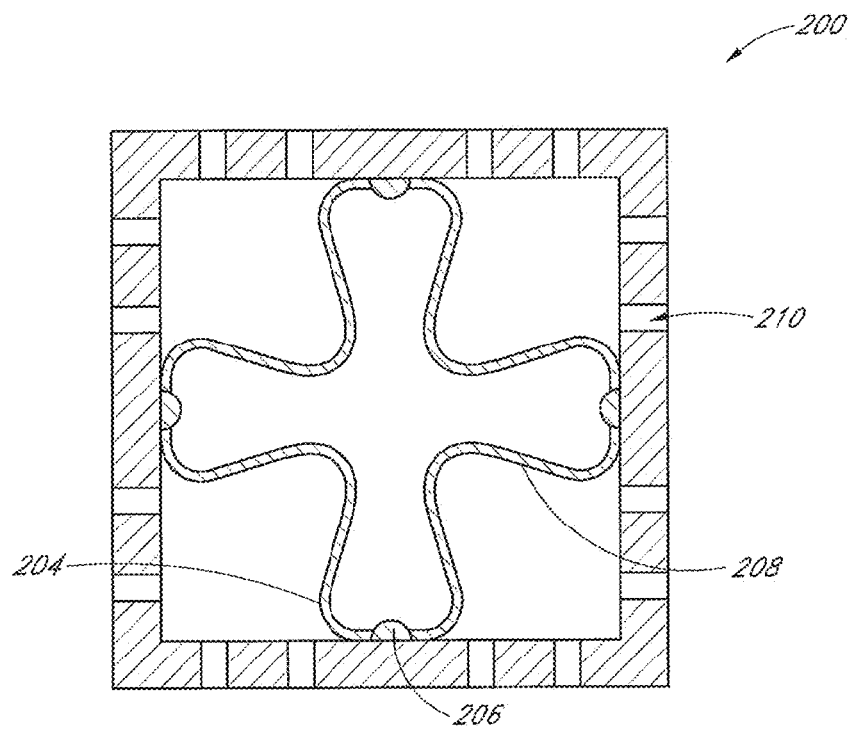
FIG. 14 is a cross-sectional top plan view of a valve with a square shaped body and posts attached towards the middle of the walls in accordance with an embodiment of the present disclosure.
Figure 15:
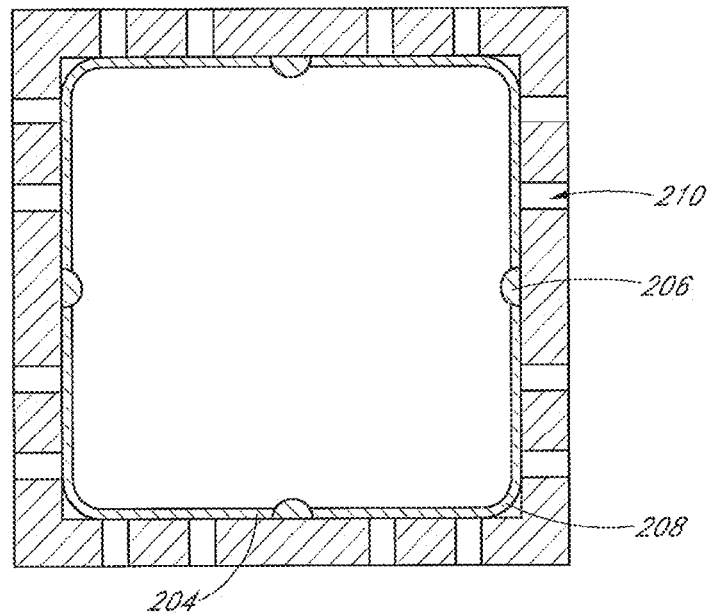
FIG. 15 is a cross-sectional top plan view of the valve of FIG. 14, in the closed configuration.

FIG. 14 illustrates a cross-sectional view of a valve 200 having a square shaped body. The internal member 204 is attached to the body with posts 206 located toward the middle of the side walls. The illustrated configuration has four posts 206 and one internal member 204. However, as discussed above in other configurations, the valve can have more than one internal member and can be attached at any number of different locations on the body in more or less than four post locations. The illustrated internal member 204 has four folds 208 that are configured to occlude ports 210 that are located toward the corners of the walls. FIG. 15 illustrates the valve 200 in a closed configuration. The folds 208 can extend around the corners of the walls to occlude the ports 210.

Figure 16:
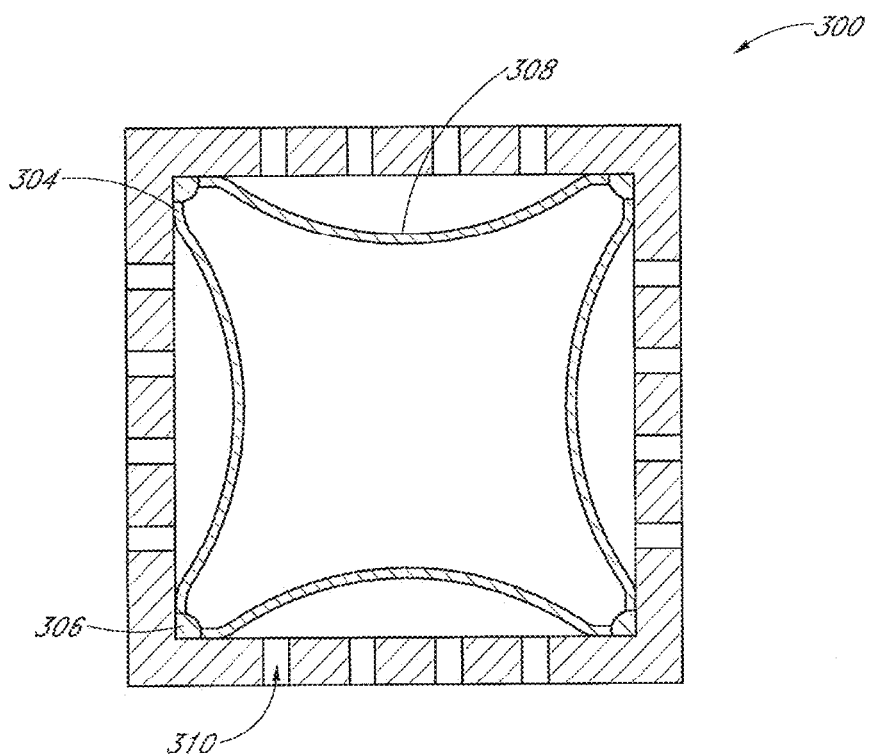
FIG. 16 is a cross-sectional top plan view of a valve with a square shaped body and posts attached at the corners of the walls in accordance with an embodiment of the present disclosure.

FIG. 16 illustrates a cross-sectional view of a valve 300 having a square shaped body, similar to FIG. 14, but with the posts 306 attached at the corners of the body. In the open configuration, the folds 308 are biased away from the walls of the body so that the ports 310 are open to the environment. In the closed configuration, as illustrated in FIG. 17, the folds 308 are against the walls of the body to occlude the ports 310. Preferably the internal member 304 is compliant so that it can compress to a shorter length in the closed configuration and extend to a longer length in the open configuration.

FIG. 18 illustrates a cross-sectional view of a valve 400 having an octagonal shaped body. The internal member 404 is attached to the body with posts 406 located at four of the corners of the side walls. The illustrated configuration has four posts 406 and one internal member 404. However, as discussed above in other configurations, the valve can have more than one internal member and can be attached at any number of different locations on the body in more or less than four post locations. The illustrated internal member 404 has four folds 408 that are configured to occlude ports 410 that are located toward the corners of the walls. FIG. 19 illustrates the valve 400 in a closed configuration. The folds 408 can extend around the corners of the walls to occlude the ports 410.

FIG. 20 illustrates a cross-sectional view of a valve 500 having a hexagonal shaped body. The internal member 504 is attached to the body with posts 506 located toward the middle of some of the side walls. The illustrated configuration has three posts 506 and one internal member 204. However, as discussed above in other configurations, the valve can have more than one internal member and can be attached at any number of different locations on the body in more or less than three post locations. The illustrated internal member 504 has three folds 508 that are configured to occlude ports 510 that are located on the walls of the body. FIG. 21 illustrates the valve 500 in a closed configuration. The folds 508 can extend around the corners of the walls to occlude the ports 510. In the illustrated configuration, each fold 508 lies against three of the walls, partially over two walls and one entire wall.

Preferred Features:

1. A valve comprising:
    a body with an interior surface defining a passageway;
    one or more ports through the body to provide fluid communication between the passageway and the environment; and
    at least one internal member attached to the body at two or more discontinuous attachment positions on the internal member, the internal member having a closed configuration that occludes the one or more ports when a gas pressure in the valve is above a threshold pressure and an open configuration that allows gas to pass from the passageway to the environment when the gas pressure in the valve is at or below a threshold pressure.

2. The valve of paragraph 1, wherein the interior surface is curved.

3. The valve of paragraph 1 or paragraph 2, wherein the at least one internal member moves in a direction that is substantially perpendicular to the direction of gases flow through the valve.

4. The valve of any one of the preceding paragraphs, wherein the at least one internal member is configured to progressively roll over the interior surface of the body.

5. The valve of any one of the preceding paragraphs, wherein the at least one internal member transitions between the open configuration and the closed configuration at a distinct threshold pressure.

6. The valve of any one of the paragraphs 1-4, wherein the at least one internal member transitions between the open configuration and the closed configuration during a range of pressures.

7. The valve of paragraph 6, wherein the range of pressures is at least approximately 2 cm H2O and/or less than or equal to approximately 3 cm H2O.

8. The valve of paragraph 6, wherein the range of pressures is at least approximately 1.5 cm H2O and/or less than or equal to approximately 4 cm H2O.

9. The valve of any one of the preceding paragraphs, wherein the one or more ports is located at generally the same position along the length of the valve as the at least one internal member.

10. The valve of any one of the preceding paragraphs, wherein the body is a round or oval tube and the at least one internal member extends around at least part of an inner circumference of the body in the closed configuration.

11. The valve of paragraph 10, wherein the one or more ports are disposed around part of the circumference of the body.

12. The valve of paragraph 10, wherein the one or more ports are disposed around the entire circumference of the body.

13. The valve of any one of the preceding paragraphs, wherein the one or more ports are circular holes having a diameter of approximately 1 mm.

14. The valve of any one of the preceding paragraphs, wherein the one or more ports have a combined venting area of at least approximately 30 mm$^2$ and/or less than or equal to approximately 600 mm$^2$.

15. The valve of any one of the preceding paragraphs, wherein the one or more ports have a combined venting area of approximately 40 mm$^2$.

16. The valve of any one of the preceding paragraphs, wherein the threshold pressure is approximately 2 cm H2O.

17. The valve of any one of the preceding paragraphs, wherein a length of the at least one internal member between attachment positions is approximately the same as a length of the interior surface of the body between the attachment positions.

18. The valve of any one of the preceding paragraphs, wherein the at least one internal member is a continuous member configured to extend around the interior surface of the body in the closed configuration.

19. The valve of any one of the preceding paragraphs, wherein the valve is configured to be placed at an inlet of a patient interface.

20. The valve of any one of the preceding paragraphs, wherein the valve is configured to be placed in-line between a patient interface and a blower.

21. The valve of any one of the preceding paragraphs, wherein the at least one internal member is attached to the body by posts that extend through the body.

22. The valve of any one of paragraphs 1-20, wherein the at least one internal member is attached to the body by an adhesive.

23. The valve of any one of paragraphs 1-20, wherein the at least one internal member is attached by overmoulding onto the body.

24. The valve of any one of the preceding paragraphs, wherein the valve is an anti-asphyxia valve.

25. The valve of any one of paragraphs 1-23, wherein the valve is a constant flow valve.

26. The valve of paragraph 25, wherein the at least one internal member transitions between the open configuration and the closed configuration during pressures ranging from at least approximately 0 cm H2O and/or less than or equal to approximately 20 cm H2O.

27. A valve comprising:
a body with an interior surface defining a passageway, the body configured to be positioned in-line with a flow of respiratory gases;
one or more ports through the body to provide fluid communication between the passageway and the environment, the one or more ports disposed around at least part of a circumference of the body; and
at least one internal member attached to the body at two or more discontinuous attachment positions on the internal member, the attachment positions being generally at the same location along the length of the valve as the one or more ports;
wherein the at least one internal member is in an open configuration that allows gas to pass from the passageway to the environment when the gas pressure in the valve is at or below a threshold pressure, the at least one internal member being biased radially inward away from the interior surface;
wherein the at least one internal member is in a closed configuration that occludes the one or more ports when a gas pressure in the valve is above a threshold pressure, the at least one internal member moving radially outward toward the interior surface to occlude the one or more ports.

28. The valve of paragraph 27, wherein the interior surface is curved.

29. The valve of paragraph 27 or paragraph 28, wherein the body is round.

30. The valve of any one of paragraphs 27-29, wherein the at least one internal member moves in a direction that is substantially perpendicular to the direction of gases flow through the valve.

31. The valve of any one of paragraphs 27-30, wherein the at least one internal member is configured to progressively roll over the interior surface of the body.

32. The valve of any one of paragraphs 27-31, wherein the at least one internal member transitions between the open configuration and the closed configuration at a distinct threshold pressure.

33. The valve of any one of paragraphs 27-31, wherein the at least one internal member transitions between the open configuration and the closed configuration during a range of pressures.

34. The valve of paragraph 33, wherein the range of pressures is at least approximately 2 cm H2O and/or less than or equal to approximately 3 cm H2O.

35. The valve of paragraph 33, wherein the range of pressures is at least approximately 1.5 cm H2O and/or less than or equal to approximately 4 cm H2O.

36. The valve of any one of paragraphs 27-35, wherein the one or more ports are disposed around the entire circumference of the body.

37. The valve of any one of paragraphs 27-36, wherein the one or more ports are circular holes having a diameter of approximately 1 mm.

38. The valve of any one of paragraphs 27-37, wherein the one or more ports have a combined venting area of at least approximately 30 mm$^2$ and/or less than or equal to approximately 600 mm$^2$.

39. The valve of any one of paragraphs 27-38, wherein the one or more ports have a combined venting area of approximately 40 mm².

40. The valve of any one of paragraphs 27-39, wherein the threshold pressure is approximately 2 cm H2O.

41. The valve of any one of paragraphs 27-40, wherein a length of the at least one internal member between attachment positions is approximately the same as a length of the interior surface of the body between the attachment positions.

42. The valve of any one of paragraphs 27-41, wherein the at least one internal member is a continuous member configured to extend around the interior surface of the body in the closed configuration.

43. The valve of any one of paragraphs 27-42, wherein the valve is configured to be placed at an inlet of a patient interface.

44. The valve of any one of paragraphs 27-43, wherein the valve is configured to be placed in-line between a patient interface and a blower.

45. The valve of any one of paragraphs 27-44, wherein the at least one internal member is attached to the body by posts that extend through the body.

46. The valve of any one of paragraphs 27-44, wherein the at least one internal member is attached to the body by an adhesive.

47. The valve of any one of paragraphs 27-44, wherein the at least one internal member is attached by overmoulding onto the body.

48. The valve of any one of paragraphs 27-47, wherein the valve is an anti-asphyxia valve.

49. The valve of any one of paragraphs 27-47, wherein the valve is a constant flow valve.

50. The valve of paragraph 49, wherein the at least one internal member transitions between the open configuration and the closed configuration during pressures ranging from at least approximately 0 cm H2O and/or less than or equal to approximately 20 cm H2O.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to."

Where, in the foregoing description reference has been made to integers or components having known equivalents thereof, those integers are herein incorporated as if individually set forth.

The invention may also be said broadly to consist in the parts, elements and features referred to or indicated in the specification of the application, individually or collectively, in any or all combinations of two or more of said parts, elements or features.

Reference to any prior art in this specification is not, and should not be taken as, an acknowledgement or any form of suggestion that that prior art forms part of the common general knowledge in the field of endeavour in any country in the world.

Certain features, aspects and advantages of an embodiment of the present invention have been described with reference to a CPAP apparatus, particularly for use in the treatment of obstructive sleep apnea. However, certain features, aspects and advantages of the valve as described above may be advantageously used with other therapeutic or non-therapeutic breathing devices, such as non-invasive ventilators, or for the treatment of other conditions, such as COPD. Certain features, aspects and advantages of the method and apparatus of the present disclosure may be equally applied to other breathing devices for other conditions.

Although the present inventions have been described in terms of certain embodiments or configurations, other embodiments apparent to those of ordinary skill in the art also are within the scope of these inventions. Thus, various changes and modifications may be made without departing from the spirit and scope of the inventions. For instance, various components may be repositioned as desired. Moreover, not all of the features, aspects and advantages are necessarily required to practice the present inventions. Accordingly, the scope of the present inventions is intended to be defined only by the claims that follow.

What is claimed is:

1. A valve configured for use in positive airway pressure therapy, the valve comprising:
    a tubular body with an interior surface and an exterior surface, the interior surface surrounding a passageway through which fluids can flow;
    one or more ports comprising through holes in the tubular body that extend from the interior surface to the exterior surface such that the passageway is in fluid communication with an environment through the one or more ports;
    at least one internal member attached to the tubular body at two or more discontinuous attachment positions on the at least one internal member;
    wherein the at least one internal member comprises an elongate ribbon that is opposed to the one or more ports of the valve, the at least one internal member having an open configuration in which the elongate ribbon curves away from the interior surface of the tubular body and a closed configuration in which the elongate ribbon abuts the interior surface to occlude the one or more ports; and
    wherein the two or more discontinuous attachment positions are evenly spaced around a circumference of the at least one internal member.

2. The valve of claim 1, wherein the interior surface is curved.

3. The valve of claim 1, wherein the interior surface is curved, and wherein the elongate ribbon curves with the interior surface in the closed configuration of the at least one internal member.

4. The valve of claim 1, wherein the at least one internal member is configured to progressively roll over the interior surface of the tubular body.

5. The valve of claim 1, wherein the at least one internal member transitions between the open configuration and the closed configuration at a distinct threshold pressure within the tubular body.

6. The valve of claim 1, wherein the one or more ports are circular holes having a diameter of approximately 1 mm.

7. The valve of claim 1, wherein the one or more ports have a combined venting area of at least approximately 30 mm² and/or less than or equal to approximately 600 mm².

8. The valve of claim 1, wherein a threshold pressure within the tubular body is approximately 2 cm $H_2O$.

9. The valve of claim 1, wherein a length of the at least one internal member between attachment positions is approximately the same as a length of the interior surface of the tubular body between the attachment positions.

10. The valve of claim 1, wherein the at least one internal member is a continuous member configured to extend around the interior surface of the tubular body in the closed configuration.

11. The valve of claim 1, wherein the valve is configured to be placed at an inlet of a patient interface.

12. The valve of claim 1, wherein the valve is configured to be placed in-line between a patient interface and a blower.

13. The valve of claim 1, wherein the at least one internal member is attached to the tubular body by posts that extend through the tubular body.

14. The valve of claim 1, wherein the at least one internal member is attached to the tubular body by an adhesive or by overmoulding onto the tubular body.

15. The valve of claim 1, wherein the valve is a constant flow valve.

16. The valve of claim 1, wherein the at least one internal member is configured to be in the open configuration when gas flow pressure in the valve is below a threshold pressure within the tubular body.

17. The valve of claim 1, wherein fluids can flow from a first end of the tubular body to a second end of the tubular body when the at least one internal member is in the open configuration and when the at least one internal member is in the closed configuration.

18. The valve of claim 1, wherein the at least one internal member transitions between the open configuration and the closed configuration during a range of pressures within the tubular body.

19. The valve of claim 18, wherein the range of pressures is at least approximately 1.5 cm $H_2O$ and/or less than or equal to approximately 4 cm $H_2O$.

20. A valve configured for use in positive airway pressure therapy, the valve comprising:
- a tubular body with an interior surface and an exterior surface, the interior surface surrounding a passageway through which fluids can flow;
- one or more ports comprising through holes in the tubular body that extend from the interior surface to the exterior surface such that the passageway is in fluid communication with an environment through the one or more ports;
- at least one internal member attached to the tubular body at two or more discontinuous attachment positions on the at least one internal member;
- wherein the at least one internal member comprises an elongate ribbon that is opposed to the one or more ports of the valve, the at least one internal member having an open configuration in which the elongate ribbon curves away from the interior surface of the tubular body and a closed configuration in which the elongate ribbon abuts the interior surface to occlude the one or more ports;
- wherein movement of the elongate ribbon is in a direction perpendicular to a flow of air through the tubular body; and
- wherein the two or more discontinuous attachment positions are evenly spaced around a circumference of the at least one internal member.

* * * * *